United States Patent
Eom et al.

(10) Patent No.: US 9,914,682 B2
(45) Date of Patent: Mar. 13, 2018

(54) HIGHLY EFFICIENT NEOPENTYL GLYCOL PREPARATION METHOD AND DEVICE THEREFOR

(71) Applicant: LG CHEM, LTD., Seoul (KR)

(72) Inventors: Sung Shik Eom, Daejeon (KR); Dong Hyun Ko, Daejeon (KR); Mi Young Kim, Daejeon (KR); Da Won Jung, Daejeon (KR); Tae Yun Kim, Daejeon (KR); Min Ji Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/906,155

(22) PCT Filed: Sep. 15, 2015

(86) PCT No.: PCT/KR2015/009661
§ 371 (c)(1),
(2) Date: Jan. 19, 2016

(87) PCT Pub. No.: WO2016/047957
PCT Pub. Date: Mar. 31, 2016

(65) Prior Publication Data
US 2016/0229772 A1    Aug. 11, 2016

(30) Foreign Application Priority Data

Sep. 25, 2014  (KR) .......................... 10-2014-0128324
Sep. 14, 2015  (KR) .......................... 10-2015-0129657

(51) Int. Cl.
*C07C 29/141*    (2006.01)
*B01J 23/78*    (2006.01)
(Continued)

(52) U.S. Cl.
CPC .............. *C07C 29/141* (2013.01); *B01J 19/24* (2013.01); *B01J 21/08* (2013.01); *B01J 23/78* (2013.01); *B01J 2219/00103* (2013.01)

(58) Field of Classification Search
CPC ..................... C07C 29/141; B01J 23/78; B01J 2219/00103; B01J 2219/24; B01J 19/24
See application file for complete search history.

(56) References Cited

U.S. PATENT DOCUMENTS

| 4,855,515 A | 8/1989 | Morris et al. |
| 6,201,159 B1 * | 3/2001 | Choi ..................... C07C 29/141 568/853 |

(Continued)

FOREIGN PATENT DOCUMENTS

| CN | 102249854 A | 11/2011 |
| CN | 102884032 A | 1/2013 |

(Continued)

OTHER PUBLICATIONS

DE 102012021276 A1, Apr. 2014, pp. 1-6; English translation.*
WO2011141470A1 (English translation), Nov. 17, 2011, pp. 1-12 (Year: 2011).*

*Primary Examiner* — Medhanit W Bahta
(74) *Attorney, Agent, or Firm* — Dentons US LLP

(57) ABSTRACT

Disclosed are a highly efficient neopentyl glycol preparation method and a device therefor. The method includes adding a hydroxypivaldehyde solution and hydrogen to a hydrogenation reactor that includes a hydrogenation catalyst. The hydroxypivaldehyde solution includes 6 to 30% by weight of hydroxypivaldehyde, 35 to 70% by weight of neopentyl glycol, 10 to 30% by weight of alcohol, and 10 to 30% by weight of water.

The neopentyl glycol preparation method does not require separate heating in a section of a feed vessel to an inlet of a hydrogenation reactor unlike conventional technologies to (Continued)

save energy, and, at the same time, by-products with a high boiling point are not generated in the section to prevent poisoning of a hydrogenation catalyst in a reactor due to the by-products with a high boiling point and increase a hydrogenation yield, and a device therefor can be provided.

8 Claims, 1 Drawing Sheet

(51) Int. Cl.
*B01J 19/24* (2006.01)
*B01J 21/08* (2006.01)

(56) References Cited

U.S. PATENT DOCUMENTS

| | | | |
|---|---|---|---|
| 6,201,160 B1 * | 3/2001 | Brudermuller | B01J 21/08 |
| | | | 502/305 |
| 6,268,539 B1 * | 7/2001 | Sen-Huang | C07C 29/141 |
| | | | 568/853 |
| 6,545,189 B1 * | 4/2003 | Nousiainen | C07C 29/141 |
| | | | 568/862 |
| 2011/0098515 A1 | 4/2011 | Schalapski et al. | |
| 2011/0184212 A1 | 7/2011 | Schulz et al. | |
| 2015/0225319 A1 * | 8/2015 | Eisenacher | B01J 23/8892 |
| | | | 568/852 |

FOREIGN PATENT DOCUMENTS

| | | | | |
|---|---|---|---|---|
| DE | 102012021276 A1 * | 4/2014 | | B01J 23/8892 |
| EP | 0484800 B1 | 9/1995 | | |
| JP | 2013-526506 A | 6/2013 | | |
| KR | 88-001560 B1 | 8/1988 | | |
| KR | 2001-0033761 A | 4/2001 | | |
| KR | 10-0366752 B1 | 5/2003 | | |
| KR | 10-2006-0073044 A | 6/2006 | | |
| WO | WO-2011141470 A1 * | 11/2011 | | C07C 29/141 |
| WO | 2014/067600 A1 | 5/2014 | | |
| WO | 2014/067602 A1 | 5/2014 | | |

* cited by examiner

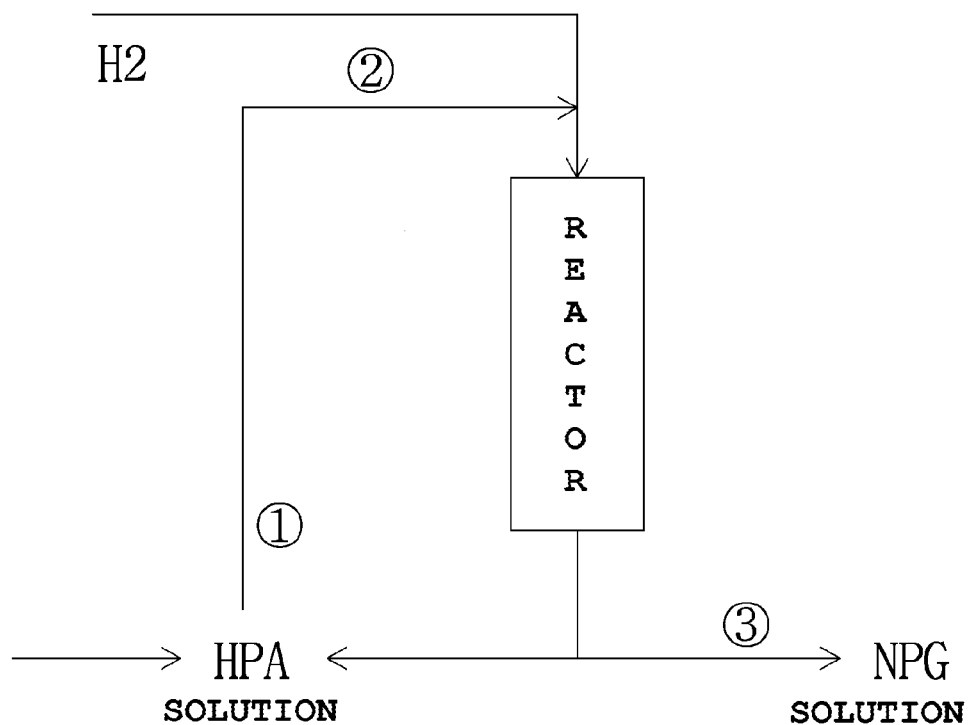

HIGHLY EFFICIENT NEOPENTYL GLYCOL PREPARATION METHOD AND DEVICE THEREFOR

CROSS-REFERENCE TO RELATED APPLICATIONS

This application is a National Stage Entry of International Application No. PCT/KR2015/009661, filed Sep. 15, 2015, and claims the benefit of and priority to Korean Application No. 10-2014-0128324, filed Sep. 25, 2014 and Korean Application No. 10-2015 -0129657, filed Sep. 14, 2015, all of which are incorporated herein by reference in their entirety for all purposes as if fully set forth herein.

TECHNICAL FIELD

The present disclosure relates to a highly efficient neopentyl glycol preparation method and a device therefor. More particularly, the present invention relates to a neopentyl glycol preparation method wherein separate heating is not required in a section of a feed vessel to an inlet of a hydrogenation reactor unlike conventional technologies to save energy, and, at the same time, by-products with a high boiling point are not generated in the section to prevent poisoning of a hydrogenation catalyst in a reactor due to the by-products with a high boiling point and increase a hydrogenation yield, and a device therefor.

BACKGROUND ART

Neopentyl glycol (NPG), a white crystalline material having a melting point of 130° C. or more, is used as an important intermediate in a variety of synthetic resins and broadly used in industries as a raw material of various plastic coating powders, synthetic lubricating oils, plasticizers, surfactants, fiber treatment agents, etc.

Such NPG is generally prepared by preparing hydroxypivaldehyde (HPA) through aldol-condensation of isobutyraldehyde and formaldehyde and then reacting the HPA with hydrogen in the presence of a catalyst.

In the reaction, high-temperature heating should be carried out such that the HPA raw material can maintain a liquid state thereof in the section of the feed vessel to the inlet of the hydrogenation reactor. Thereby, neopentyl glycol hydroxypivalate (HPNE) as a by-product with a high boiling point, is generated before the HPA raw material is fed into the hydrogenation reactor, and thus, the content of the HPA is decreased from the inlet of the hydrogenation reactor. Finally, the content of NPG generated after hydrogenation is decreased, and the contents of by-products such as HPNE are rather increased.

Like this, the process of preparing NPG through hydrogenation of HPA has problems as follows: large amounts of by-products such as esters and iso-butanol are generated due to a high-temperature operation condition. In particular, the boiling point of an ester residue such as HPNE generated through Reaction Formula 1 below is similar to that of NPG, whereby it is very difficult to perform separation through distillation and activity of a hydrogenation catalyst is decreased.

[Reaction Formula 1]

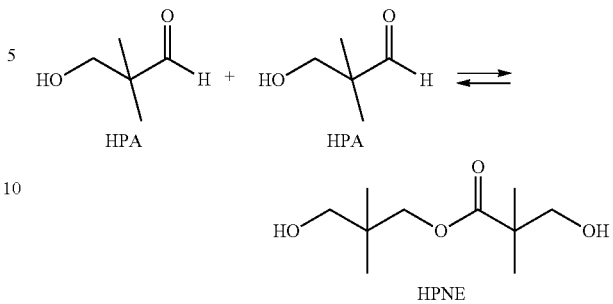

Generation rates and amounts of the by-products are known to increase with increasing temperature due to sensitivity thereof to temperature. However, complete liquefaction of an HPA raw material becomes impossible when temperature is lowered, and thus, reactivity is decreased. On the other hand, when the HPA raw material is exposed to high temperature so as to increase reactivity, by-products are greatly increased.

At present, NPG preparation technology of converting an HPA raw material present as a solid at room temperature into a liquid state by elevating temperature to about 70° C. so as to minimize generation of by-products and then feeding the HPA raw material along with a hydrogen gas into a hydrogenation reactor is known. However, the technology still has great disadvantages such as low yield and high purification costs.

RELATED DOCUMENT

Patent Document

Korean Patent Laid-Open Publication No. 2006-0073044

DISCLOSURE

Technical Problem

Therefore, the present invention has been made in view of the above problems, and it is one object of the present invention to provide a highly efficient neopentyl glycol preparation method wherein small amounts of by-products are generated without decrease of reactivity, and a device therefor.

The above and other objects can be accomplished by the present invention described below.

Technical Solution

In accordance with one aspect of the present invention, provided is a method of preparing neopentyl glycol, wherein the method includes adding a hydroxypivaldehyde solution and hydrogen to a hydrogenation reactor that including a hydrogenation catalyst, wherein the hydroxypivaldehyde solution includes 6 to 30% by weight of hydroxypivaldehyde, 35 to 70% by weight of neopentyl glycol, 10 to 30% by weight of alcohol, and 10 to 30% by weight of water.

In accordance with another aspect of the present invention, provided is a device for preparing neopentyl glycol, including a feed vessel in which a hydroxypivaldehyde solution is stored; a raw material supply pipe for supplying the hydroxypivaldehyde solution in the feed vessel to a hydrogenation reactor; a hydrogen supply pipe for supplying hydrogen to the hydrogenation reactor; the hydrogenation reactor including a hydrogenation catalyst fixed therewithin; a discharge pipe for discharging a neopentyl glycol product generated in the hydrogenation reactor; a neopentyl glycol recovery pipe for supplying a portion of the neopentyl glycol product of the discharge pipe to the feed vessel; a recycle pipe for recycling a portion of the neopentyl glycol product of the discharge pipe in the hydrogenation reactor; and a heating unit for heating, immediately before being fed to the hydrogenation reactor, the hydroxypivaldehyde solution supplied to the hydrogenation reactor via the raw material supply pipe.

Advantageous Effects

As apparent from the fore-going, the present invention advantageously provides a neopentyl glycol preparation method wherein separate heating is not required in a section of a feed vessel to an inlet of a hydrogenation reactor unlike conventional technologies to save energy, and, at the same time, by-products with a high boiling point are not generated in the section to prevent poisoning of a hydrogenation catalyst in a reactor due to the by-products with a high boiling point and greatly increase a hydrogenation yield, and a device therefor.

BRIEF DESCRIPTION OF THE DRAWINGS

The FIGURE is a flowchart schematically illustrating a neopentyl glycol preparation process of the present disclosure.

BEST MODE

Now, the present invention will be described in more detail.

A method of preparing neopentyl glycol according to the present disclosure includes adding a hydroxypivaldehyde solution and hydrogen to a hydrogenation reactor that including a hydrogenation catalyst, wherein the hydroxypivaldehyde solution includes 6 to 30% by weight of hydroxypivaldehyde, 35 to 70% by weight of neopentyl glycol, 10 to 30% by weight of alcohol, and 10 to 30% by weight of water. In this case, since separate heating is not required in a section of a feed vessel to an inlet of a hydrogenation reactor, energy can be saved, and, at the same time, by-products with a high boiling point are not generated. Furthermore, poisoning of a hydrogenation catalyst in a reactor due to the by-products with a high boiling point and activity of the hydrogenation catalyst can be protected. As a result, a hydrogenation yield is greatly enhanced.

In the present disclosure, the feed vessel is not specifically limited so long as it may store a raw material therein and supply the same to a raw material supply pipe. The feed vessel may be, for example, a raw material storage tank, a raw material supply tank, a feed tank, or the like.

In an embodiment, the feed vessel may further include a stirrer for mixing raw materials.

The hydroxypivaldehyde solution may include, for example, 8 to 20% by weight of hydroxypivaldehyde, 40 to 52% by weight of neopentyl glycol, 15 to 25% by weight of alcohol, and 10 to 27% by weight of water. In this case, the amount of by-products is decreased without decrease of reactivity.

A weight ratio of the hydroxypivaldehyde to the neopentyl glycol may be, for example, 1:1.5 to 1:8, or 1:2 to 1:6.5. Within this range, heat removal is easily performed, whereby reaction is satisfactorily carried out and the amount of by-products is decreased.

The alcohol may be, for example, octanol, iso-butanol, methanol, or the like. Preferably, the alcohol is octanol.

The amount of the water may be, for example, 10 to 30% by weight, 10 to 27% by weight, or 12 to 30% by weight. Within this range, superior reactivity, HPA conversion rate, and NPG yield are exhibited.

In an embodiment, the neopentyl glycol may be a portion of neopentyl glycol discharged from the hydrogenation reactor. In this case, since a material equal to a reaction product is used, a separation process is not separately required in a post-treatment process. Accordingly, superior economic feasibility and process efficiency are exhibited.

In an embodiment, the temperature of the hydroxypivaldehyde solution is maintained to 40 to 100° C., or 60 to 75° C. from the feed vessel and supplied to the hydrogenation reactor. When the temperature is low, the raw material solution is solidified and thus there may be problems in transferring the raw material solution. When the temperature is more highly maintained, by-products are generated in the feed vessel. Therefore, when the temperature is properly maintained, generation of by-products may be suppressed and a reaction yield may be increased. The temperature of the feed vessel may be easily accomplished by feeding a high-temperature NPG product discharged from the hydrogenation reactor into the feed vessel in a constant ratio (mixing with hydroxypivaldehyde).

In an embodiment, the hydroxypivaldehyde solution may be dispersion-fed, by means of a distributor, into the hydrogenation reactor. In this case, superior reaction yield, HPA conversion rate, and NPG selectivity are exhibited.

Interior temperature of the hydrogenation reactor, i.e., reaction temperature or the temperature of the reactor inlet, may be, for example, 100 to 250° C., 130 to 200° C., or 140 to 195° C.

Interior pressure of the hydrogenation reactor, i.e., reaction pressure, may be, for example, 10 to 250 bar, 20 to 120 bar, or 25 to 50 bar.

The hydrogenation catalyst may be, for example, a copper-based catalyst.

The copper-based catalyst may be, for example, a CuO/BaO catalyst. In this case, superior catalyst performance and long lifespan are exhibited.

The CuO/BaO catalyst preferably includes 60 to 99% by weight of CuO and 1 to 40% by weight of BaO, more preferably 80 to 95% by weight of CuO and 5 to 20% by weight of BaO, most preferably 85 to 90% by weight of CuO and 10 to 15% by weight of BaO. Within this range, superior catalyst performance and long lifespan are exhibited.

The contents of metals and metal oxides in the CuO/BaO catalyst may be, for example, measured thorough ICP analysis.

The copper-based catalyst may include, for example, a silicon oxide or aluminum oxide supporter. In this case, a catalyst exhibits superior performance and properties, and activity thereof is maintained for a long time.

The copper-based catalyst may be particularly a CuO/BaO/SiO catalyst.

The CuO/BaO/SiO catalyst may be, for example, (CuO)x(BaO)y(SiO)z, where x:y:z=10 to 50:0 to 10:40 to 90, 10 to 50:1 to 10:40 to 89, or 29 to 50:1 to 10:40 to 70, in % by weight. The total of x and y is 20 to 50% by weight or 30 to 50% by weight, based on 100% by weight of the total of x, y, and z. Within this range, superior catalyst performance and long lifespan are exhibited.

The hydrogenation reactor may be, for example, a fixed bed reactor. In this case, the catalyst may be easily separated from the reaction product, the catalyst may be easily replaced, and the size of the reactor may be reduced. Accordingly, an economically efficient process may be provided.

In an embodiment, the hydroxypivaldehyde solution is preferably prepared in the feed vessel and supplied to the hydrogenation reactor. In this case, total preparation process may be stably operated and operations may be easily performed.

The expression "hydroxypivaldehyde solution is prepared in a feed vessel" means that a hydroxypivaldehyde solution with a desired composition is not prepared while the raw material is supplied to the raw material supply pipe, and a hydroxypivaldehyde solution is supplied to the hydrogenation reactor via the raw material supply pipe after preparation of the hydroxypivaldehyde solution with a desired composition in the feed vessel.

In the neopentyl glycol solution discharged from the hydrogenation reactor, an ingredient with a boiling point higher than that of NPG may be included in an amount of, for example, 6% by weight or less or 5.5% by weight or less. In this case, purification equipment is simple and purification costs are low. The ingredient with a high boiling point may be, for example, a hydroxypivaldehyde dimer, i.e., HPNE.

In an embodiment, the hydroxypivaldehyde solution may be mixed with hydrogen gas before being supplied to the hydrogenation reactor. In this case, the dispersion efficiency of a gas-type or liquid-type raw material fed to the reactor may be increased, whereby an HPA conversion rate and an NPG yield may be increased.

In an embodiment, a portion of a neopentyl glycol solution discharged from the hydrogenation reactor may be recycled in the hydrogenation reactor. In this case, heat generated by the hydrogenation may be easily controlled by combining a heat exchanger therewith.

In an embodiment, the hydroxypivaldehyde solution may be heated up to about a hydrogenation temperature, by a heating means or unit, immediately before being fed into the hydrogenation reactor. In this case, a superior HPA conversion rate and hydrogenation yield is exhibited.

The heating means or unit is not specifically limited so long as it can be applied to conventional hydrogenation devices for hydroxypivaldehyde solutions.

The expression "immediately before being fed to the hydrogenation reactor" may mean that a section between a point where the hydroxypivaldehyde solution and the recycled neopentyl glycol solution meet and the hydrogenation reactor, or between a connection part of the raw material supply pipe and the recycle pipe and the hydrogenation reactor.

The hydrogenation may be performed at, for example, about 50 to 200° C., 60 to 180° C., or 80 to 145° C.

In an embodiment, heating may be not separately performed in a section of a feed vessel to an inlet of the hydrogenation reactor. In this case, generation of by-products may be suppressed in a process for supplying to a reactor while preventing solidification of a raw material for reaction.

A device for preparing neopentyl glycol according to the present disclosure includes a feed vessel in which a hydroxypivaldehyde solution is stored; a raw material supply pipe for supplying the hydroxypivaldehyde solution in the feed vessel to a hydrogenation reactor; a hydrogen supply pipe for supplying hydrogen to the hydrogenation reactor; the hydrogenation reactor including a hydrogenation catalyst fixed therewithin; a discharge pipe for discharging a neopentyl glycol product generated in the hydrogenation reactor; a neopentyl glycol recovery pipe for supplying a portion of the neopentyl glycol product of the discharge pipe to the feed vessel; a recycle pipe for recycling a portion of the neopentyl glycol product of the discharge pipe in the hydrogenation reactor; and a heating unit for heating, immediately before being fed to the hydrogenation reactor, the hydroxypivaldehyde solution supplied to the hydrogenation reactor via the raw material supply pipe.

In an embodiment, the hydrogenation reactor may include a distributor installed at a part connected to an upper hydrogen supply pipe. In this case, a reaction yield, an HPA conversion rate, and NPG selectivity are enhanced.

In an embodiment, the feed vessel may be connected to an HPA preparation device.

The FIGURE is a flowchart schematically illustrating a neopentyl glycol preparation process of the present disclosure. When the hydroxypivaldehyde (HPA) solution according to the present disclosure is used, separate heating is not required and thus energy can be saved. In addition, in ① and ② sections, by-products are not generated, and thus, poisoning of a hydrogenation catalyst due to by-products with a high boiling point such as, particularly, HPNE, can be prevented. Finally, it can be confirmed that the content of NPG, as a product of a reactor outlet ③, is greatly increased.

Now, the present invention will be described in more detail with reference to the following examples. These examples are provided only for illustration of the present invention and should not be construed as limiting the scope and spirit of the present invention.

EXAMPLES

Example 1

A hydroxypivaldehyde solution (HPA:NPG=1:4) including 12% by weight of hydroxypivaldehyde, 48% by weight of neopentyl glycol, 23.1% by weight of octanol, 12% by weight of water, and 4.5% by weight of an ingredient with a high boiling point was prepared in a feed vessel and then transferred to a 340 ml hydrogenation reactor in a flow rate of 3.4 g/min via a raw material supply pipe while maintaining the temperature of the feed vessel temperature at 60° C. At the same time, hydrogen was fed to the hydroxypivaldehyde solution of the raw material supply pipe via a hydrogen supply pipe. Here, a catalyst including CuO/BaO/SiO, where CuO:BaO:SiO=40:5:55 in a weight ratio, was fixed to the hydrogenation reactor, inlet temperature of the reactor was 140° C., and reaction pressure was 40 bar. After continuous operation over 24 hours, the neopentyl glycol product generated in the hydrogenation reactor was obtained in a discharge pipe connected to a lower part of the hydrogenation reactor. A composition of The obtained neopentyl glycol product was measured using gas chromatography (HP-1 manufactured by Agilent, measurement conditions: 70° C./3 min-10° C./min-280° C./35 min).

Example 2

An experiment was carried out in the same manner as in Example 1, except that a hydroxypivaldehyde solution (HPA:NPG=1:2) including 20% by weight of hydroxypivaldehyde, 40% by weight of neopentyl glycol, 22.9% by weight of octanol, 11.9% by weight of water, and 5.2% by weight of an ingredient with a high boiling point was used.

Example 3

An experiment was carried out in the same manner as in Example 1, except that a hydroxypivaldehyde solution (HPA:NPG=1:6.5) including 8% by weight of hydroxypivaldehyde, 52% by weight of neopentyl glycol, 22.9% by weight of octanol, 15% by weight of water, and 5.1% by weight of an ingredient with a high boiling point was used.

Comparative Example 1

An experiment was carried out in the same manner as in Example 1, except that a hydroxypivaldehyde solution (HPA:NPG=1:11) including 5% by weight of hydroxypivaldehyde, 55% by weight of neopentyl glycol, 23% by weight of octanol, 12.2% by weight of water, and 4.8% by weight of an ingredient with a high boiling point was used.

Comparative Example 2

An experiment was carried out in the same manner as in Example 1, except that a hydroxypivaldehyde solution (HPA:NPG=1:1.4) including 35% by weight of hydroxypivaldehyde, 25% by weight of neopentyl glycol, 23% by weight of octanol, 12% by weight of water, and 5% by weight of an ingredient with a high boiling point was used.

[Test Examples]

Neopentyl glycol products obtained according to Examples 1 to 3 and Comparative Examples 1 to 2 were subjected to gas chromatography, and HPA conversion rates and NPG yields thereof were calculated as described below. Results are summarized in Table 1 below.

Conversion rate: (1-(HPA content in product/HPA content in raw material))*100

Yield: (NPG content in product/HPA content in raw material+NPG content in raw material))*100

Ingredients with high boiling point: HPNE with a boiling point higher than that of NPG is included in an amount of 3 to 3.5% by weight and the other ingredients with a boiling point higher than that of NPG were not identified.

TABLE 1

| Classification | | Example 1 | Example 2 | Example 3 | Comparative Example 1 | Comparative Example 2 |
|---|---|---|---|---|---|---|
| HPA Solution composition | NPG | 48 | 40 | 52 | 55 | 34.5 |
| | HPA | 12 | 20 | 8 | 5 | 25.5 |
| | 2-EH + $H_2O$ | 35.1 | 34.8 | 34.9 | 35.2 | 35 |
| | Ingredient with high boiling point | 4.9 | 5.2 | 5.1 | 4.8 | 5 |
| NPG Solution composition | NPG | 59.8 | 59.5 | 59.7 | 57 | 56 |
| | HPA | 0.1 | 0.04 | 0.08 | 0.3 | 1 |
| | 2-EH + $H_2O$ | 35 | 35 | 35 | 35 | 35 |
| | Ingredient with high boiling point | 5.1 | 5.46 | 5.22 | 7.7 | 8 |//

TABLE 1-continued

| Classification | Example 1 | Example 2 | Example 3 | Comparative Example 1 | Comparative Example 2 |
|---|---|---|---|---|---|
| HPA conversion rate (%) | 99.2 | 99.8 | 99.0 | 94.0 | 96.1 |
| NPG yield (%) | 99.7 | 99.2 | 99.5 | 95.0 | 93.3 |

As shown in Table 1, it can be confirmed that, when the neopentyl glycol preparation method (Examples 1 to 3) according to the present disclosure is used, superior HPA conversion rate and NPG reaction yield are exhibited and, particularly, the neopentyl glycol products obtained according to the method hardly have any by-products (newly added ingredients with a high boiling point).

The invention claimed is:

1. A method of preparing neopentyl glycol, wherein the method comprises:
   preparing a hydroxypivaldehyde solution in a feed vessel; and
   supplying hydrogen and the hydroxypivaldehyde solution to a hydrogenation reactor comprising a hydrogenation catalyst,
   wherein the hydroxypivaldehyde solution is not heated during transport of the hydroxypivaldehyde solution from a section of the feed vessel to an inlet of the hydrogenation reactor,
   wherein the temperature of the feed vessel is maintained at a range of 60° C. to 75° C.,
   wherein the hydroxypivaldehyde solution comprises 8 to 20% by weight of hydroxypivaldehyde, 40 to 52% by weight of neopentyl glycol, 15 to 25% by weight of alcohol, and 12 to 30% by weight of water, wherein a weight ratio of the hydroxypivaldehyde to the neopentyl glycol is 1:2 to 1:6.5, and
   wherein the hydrogenation catalyst is of the formula $(CuO)_x(BaO)_y(SiO)_z$, where x:y:z=10 to 50:1 to 10:40 to 90% by weight, and wherein x+y is 20 to 50% by weight, based on 100% by weight of the total of x, y and z.

2. The method according to claim 1, wherein a portion of the neopentyl glycol discharged from the hydrogenation reactor is added to the hydroxypivaldehyde solution.

3. The method according to claim 1, wherein interior temperature of the hydrogenation reactor is 100 to 250° C.

4. The method according to claim 1, wherein the hydrogenation reactor is a fixed bed reactor.

5. The method according to claim 1, wherein a neopentyl glycol solution discharged from the hydrogenation reactor comprises 6.0% by weight or less of neopentyl glycol hydroxypivalate (HPNE).

6. The method according to claim 1, wherein the hydroxypivaldehyde solution is mixed with hydrogen gas before being supplied to the hydrogenation reactor.

7. The method according to claim 1, wherein a portion of a neopentyl glycol solution discharged from the hydrogenation reactor is recycled in the hydrogenation reactor.

8. The method according to claim 1, wherein the hydroxypivaldehyde solution is heated up to hydrogenation temperature immediately before being fed into the hydrogenation reactor.

* * * * *